(12) United States Patent
Leivseth et al.

(10) Patent No.: US 11,844,736 B2
(45) Date of Patent: Dec. 19, 2023

(54) APPARATUS, SYSTEM, AND METHOD FOR TISSUE REGENERATION

(71) Applicant: PELVITAL USA, INC., Minneapolis, MN (US)

(72) Inventors: Gunnar Leivseth, Oslo (NO); Ole Jakob Olsen, Stathelle (NO); Dale Wahlstrom, Apple Valley, MN (US); Luke Dery, Brooklyn Park, MN (US)

(73) Assignee: Pelvital USA, Inc., Minneapolis, MN (US)

( * ) Notice: Subject to any disclaimer, the term of this patent is extended or adjusted under 35 U.S.C. 154(b) by 536 days.

(21) Appl. No.: 16/772,744

(22) PCT Filed: Dec. 12, 2018

(86) PCT No.: PCT/US2018/065132
§ 371 (c)(1),
(2) Date: Jun. 12, 2020

(87) PCT Pub. No.: WO2019/118561
PCT Pub. Date: Jun. 20, 2019

(65) Prior Publication Data
US 2020/0337941 A1    Oct. 29, 2020

Related U.S. Application Data

(60) Provisional application No. 62/597,934, filed on Dec. 13, 2017.

(51) Int. Cl.
*A61N 1/36* (2006.01)
*A61H 21/00* (2006.01)
*A61H 19/00* (2006.01)

(52) U.S. Cl.
CPC ............. *A61H 21/00* (2013.01); *A61H 19/40* (2013.01); *A61N 1/36007* (2013.01); *A61H 2201/10* (2013.01); *A61H 2201/5015* (2013.01); *A61H 2201/5043* (2013.01); *A61H 2201/5048* (2013.01); *A61H 2201/5061* (2013.01);
(Continued)

(58) Field of Classification Search
CPC .... A61H 21/00; A61H 19/40; A61H 2201/10; A61H 2201/5015; A61H 2201/5043; A61H 2201/5048; A61H 2201/5061; A61H 2201/5084; A61H 2201/5097; A61H 2230/605; A61H 2201/0165; A61H 2201/1207; A61H 2201/5007; A61H 2201/5012; A61H 2205/06; A61H 2205/081; A61H 2205/083; A61H 2205/084; A61H 2205/087; A61H 2205/10; A61H 2230/60; A61H 19/00;
(Continued)

(56) References Cited

U.S. PATENT DOCUMENTS 5,483,832 A    1/1996  Pauser et al.
5,674,238 A   10/1997  Sample et al.
(Continued)

FOREIGN PATENT DOCUMENTS

CN    204890012 U    12/2015

*Primary Examiner* — Amanda K Hulbert
*Assistant Examiner* — Natasha Patel
(74) *Attorney, Agent, or Firm* — Skaar Ulbrich Macari, PA (57) ABSTRACT

An apparatus, system, and method for the regeneration of tissue by pre-tensioning of tissue prior to or in conjunction with the application of mechanotransduction therapy.

20 Claims, 9 Drawing Sheets

(52) U.S. Cl.
 CPC ........... *A61H 2201/5084* (2013.01); *A61H 2201/5097* (2013.01); *A61H 2230/605* (2013.01)

(58) Field of Classification Search
 CPC ........... A61H 23/02; A61H 23/0263; A61N 1/36007; A63B 2220/51; A63B 23/20
 See application file for complete search history.

(56) References Cited

U.S. PATENT DOCUMENTS

| | | | |
|---|---|---|---|
| 5,733,230 A | 3/1998 | Sawchuck et al. | |
| 5,766,137 A | 6/1998 | Omata | |
| 5,782,745 A | 7/1998 | Benderev | |
| 5,881,731 A | 3/1999 | Remes | |
| 6,030,338 A | 2/2000 | Benderev | |
| 6,110,099 A | 8/2000 | Benderev | |
| 6,165,141 A | 12/2000 | Muller et al. | |
| 6,244,066 B1 | 6/2001 | LaRose | |
| 6,428,467 B1 | 8/2002 | Benderev | |
| 6,741,895 B1 | 5/2004 | Gafni et al. | |
| 6,905,471 B2 | 6/2005 | Leivseth et al. | |
| 6,923,773 B2 | 8/2005 | Leivseth et al. | |
| 7,338,417 B2 | 3/2008 | Kang et al. | |
| 7,998,202 B2 | 8/2011 | Lesh | |
| 8,186,217 B2 | 5/2012 | Veltink | |
| 8,360,954 B2 | 1/2013 | Kim | |
| 8,369,953 B2 | 2/2013 | Peddicord | |
| 8,485,179 B1 | 7/2013 | Meyer et al. | |
| D710,007 S | 7/2014 | Cornelius | |
| 8,784,345 B2 | 7/2014 | Peddicord | |
| 8,805,472 B2 | 8/2014 | Iglesias | |
| 8,818,512 B2 | 8/2014 | Peddicord | |
| 8,840,571 B2 | 9/2014 | Egorov et al. | |
| 8,870,724 B2 | 10/2014 | Armitage et al. | |
| 9,220,855 B2 | 12/2015 | Meyer et al. | |
| 9,439,830 B2 | 9/2016 | Norton | |
| 9,655,808 B2 | 5/2017 | Peddicord | |
| 9,776,040 B2 | 10/2017 | Sedic | |
| 9,844,681 B2 | 12/2017 | Kim et al. | |
| 9,878,207 B2 | 1/2018 | Brinkhaus et al. | |
| 9,949,888 B2 | 4/2018 | Leivseth et al. | |
| 9,950,128 B2 | 4/2018 | Meyer et al. | |
| 10,022,293 B2 | 7/2018 | Scheuring et al. | |
| 10,039,929 B1 | 8/2018 | Schwarz et al. | |
| 10,201,702 B2 | 2/2019 | Bonde et al. | |
| 10,307,638 B2 | 6/2019 | Sedic | |
| 10,413,722 B2 | 9/2019 | Peled | |
| 10,470,862 B2 | 11/2019 | Iglesias | |
| 10,517,790 B2 | 12/2019 | Peddicord | |
| 11,166,661 B2 | 11/2021 | Daly et al. | |
| 2001/0051327 A1 | 12/2001 | Hatano et al. | |
| 2002/0120219 A1 | 8/2002 | Hovland et al. | |
| 2003/0073881 A1 | 4/2003 | Levy | |
| 2005/0256387 A1 | 11/2005 | Omata | |
| 2006/0036188 A1 | 2/2006 | Hoffman et al. | |
| 2007/0112284 A1* | 5/2007 | Hoffman | A61B 5/053 128/905 |
| 2007/0287610 A1 | 12/2007 | Novak et al. | |
| 2008/0058887 A1* | 3/2008 | Griffin | A61N 1/36007 607/40 |
| 2009/0056445 A1 | 3/2009 | Veltink et al. | |
| 2009/0093673 A1 | 4/2009 | Lee et al. | |
| 2009/0281483 A1* | 11/2009 | Baker | A61M 11/00 604/35 |
| 2010/0174214 A1 | 7/2010 | Gabbay et al. | |
| 2010/0174218 A1 | 7/2010 | Shim | |
| 2010/0262049 A1 | 10/2010 | Novak et al. | |
| 2012/0053017 A1 | 3/2012 | Kushnir | |
| 2013/0184567 A1 | 7/2013 | Xie et al. | |
| 2014/0257268 A1 | 9/2014 | Sachs et al. | |
| 2014/0296705 A1 | 10/2014 | Iglesias | |
| 2014/0309550 A1 | 10/2014 | Iglesias | |
| 2015/0112231 A1 | 4/2015 | Iglesias | |
| 2015/0141881 A1* | 5/2015 | Oh | A61N 1/36007 607/3 |
| 2015/0165241 A1 | 6/2015 | Burdette | |
| 2015/0290453 A1 | 10/2015 | Tyler et al. | |
| 2016/0228324 A1 | 8/2016 | Garteiser et al. | |
| 2016/0338605 A1 | 11/2016 | Bastia | |
| 2016/0346610 A1 | 12/2016 | Iglesias et al. | |
| 2017/0273860 A1 | 9/2017 | Leivseth et al. | |
| 2017/0281299 A1 | 10/2017 | Iglesias | |

* cited by examiner

APPARATUS, SYSTEM, AND METHOD FOR TISSUE REGENERATION

PRIORITY

This Application is a Section 371 US National Stage Application of PCT Application No. PCT/US18/65132, filed Dec. 12, 2018, which claims priority to and the benefit of U.S. Provisional Patent Application No. 62/597,934, filed Dec. 13, 2017; with each of the identified applications and disclosures incorporated fully herein by reference.

BACKGROUND

The present invention relates to an apparatus, system, and method for regenerating tissue such as the pelvic floor musculature.

Tissues of humans and animals are able to regenerate or repair themselves and thus enable stressed, injured, or damaged tissues, that cause underlying undesirable conditions such as incontinence, to repair themselves and thus eliminate the undesirable condition. The present invention utilizes low, medium or high vibrations to create a regenerative or repair environment for tissues.

Regeneration or repair of tissue generally consists of three phases: inflammation, repair, and maturation. When a tissue is injured the cells are either quickly repaired or undergo necrosis (rupturing of the cell membrane and release of its intracellular contents). When there is an injury the body initiates or induces inflammation, which is required for the regeneration phase Inflammation causes neutrophils and macrophages to arrive at the site of the injury. Neutrophils and macrophages are responsible for the phagocytosis of dead cell debris and for the production of the anti-inflammatory cytokines required for the down-regulation of the inflammatory response that prevents further damage.

The regulation of this inflammatory response has been described in many tissues, including skeletal muscle and is ultimately responsible for the passage from an injured tissue environment to one of tissue repair. During the tissue repair process the tissue cells go through maturation, which is the last phase of regeneration. Maturation results in the consolidation of differentiated cells that acquire a functionally mature phenotype. As one might suspect, the inflammation, differentiation and maturation phases differ from tissue to tissue.

Tissues can also be repaired by the application of mechanotransduction therapy. Mechanotransduction therapy applies vibrations to the tissue in order to cause a physical change in the tissue. The mechanical forces or stress are converted by the cell into intra-cellular signaling and biochemical reactions that permit the cells of the tissue to repairs themselves.

As a mechanical stress is applied to the tissue the cytoskeleton of the tissue cells increases in stiffness in response to the forces acting on different focal adhesion sites. The cell is able to transmits the force or stress, e.g. actomyosin or other myosin motors that may generate tension in the cytoskeleton. The fibrous scaffolds are then able to transmit the stress or tension over long distances.

The mechanical stress both cause deformation nuclear envelope, other stress sensing structures within cells and on the surrounding extracellular matrix (ECM). The cell then activate gene expression, produce new proteins and remodels the ECM that comprises its tissue microenvironment in a load-dependent manner. As the ECM microenvironment changes to repair the cell, the viscoelasticity properties of the tissue is repaired.

Any tissue may be treated by the present invention. One particular group of muscles that can be treated by the mechanotransduction properties of the present invention is the pelvic floor muscles. The pelvic floor muscles are a mind-controlled and layered muscle group which surrounds the urethra, vagina, and rectum, and which, together with the sphincter muscles, functions to control these openings. This musculature also serves to support the urethra, bladder, and uterus, as well as to resist any increases in the abdominal pressure developed during physical exertion. The muscle group includes both longitudinal muscles and annular muscles.

Training of the pelvic floor musculature has proven efficient in preventing and treating several conditions, e.g. incontinence. Numerous exercises exist for training the pelvic floor musculature. For a number of reasons, the effect of these exercises varies among people. Also, it is known that mechanical vibrations in a range below approx. 120 Hz applied to the tissue increase the training effect of such exercises. As the musculature becomes stronger, it will be possible to measure the training effect by measuring the ability of the musculature to retract.

Measuring Principle and Measurement Parameters

A stronger muscle can be expected to dampen an amplitude of oscillation applied thereto more than a weaker muscle. A first principle of measurement, therefore, may be to measure the amplitude dampening of an imposed oscillation. The measured amplitude can be described as $A \sim A_0 \sin(wt)$. A relative amplitude dampening is defined as: where $$\Delta A = (A - A_o)/A_o \qquad (1)$$

A is the amplitude measured,
$A_o$ is the amplitude imposed,
w is the angular frequency of the oscillation imposed, and
t is time.

It is considered well known to a person skilled in the art that the output signal from an accelerometer may represent an acceleration which can be integrated to obtain a velocity and a second time to obtain a displacement or deflection. It is also well known that accelerations, velocities, and displacements of equal magnitudes and opposite directions have average values of zero, and that meaningful parameters hence must be based on absolute values such as maximum acceleration, velocity, or amplitude, for example. In view of the above, it is clear that the dimensionless attenuation $\Delta A$ can be calculated from displacements in mm, velocities in m/s, accelerations in m/s2, and/or electrical signals input to the oscillator and output from the accelerometer. In any case, the attenuation $\Delta A$ can be expressed in dB, calibrated to display the force in Newton (N), etc. according to need and in manners known for persons skilled in the art.

During normal exercise, the volume of the muscle cells increases and the skeleton of the cells becomes more rigid. In another model, therefore, the pelvic floor musculature can be regarded as a visco-elastic material, i.e. as a material having properties between a fully elastic material and an entirely rigid and inelastic (viscous) material. For example, a slack or weak muscle can be expected to exhibit relatively "elastic" properties, whereas a tight or strong muscle can be expected produce more resistance and thus relatively "viscous" properties. Formally:

stress is the force acting to resist an imposed change divided by the area over which the force acts. Hence, stress is a pressure, and is measured in Pascal (Pa), and strain is the ratio between the change caused by the stress and the relaxed configuration of the object. Thus, strain is a dimensionless quantity.

The modulus of elasticity is defined as the ratio $\lambda$=stress/strain. The dynamic modulus is the same ratio when the stress arises from an imposed oscillation. When an oscillation is imposed in a purely elastic material, the elongation measured is in phase with the imposed oscillation, i.e. strain occurs simultaneously with the imposed oscillation. When the oscillation is imposed in a purely viscous material, the strain lags the stress by 90° ($\pi/2$ radians). Visco-elastic materials behave as a combination of a purely elastic and a purely viscous material. Hence, the strain lags the imposed oscillation by a phase difference between 0 and $\pi/2$.

The above can be expressed through the following equations:

$$\sigma = \sigma_o \sin(\omega t) \quad (2)$$

$$\varepsilon = \varepsilon_o \sin(\omega t - \phi) \quad (3)$$

$$\lambda = \sigma/\varepsilon \quad (4)$$

where
$\sigma$ is stress from an imposed oscillation (Pa)
$\varepsilon$ is strain (dimensionless)
$\omega$ is the oscillator frequency (Hz)
t is time(s),
$\phi$ is the phase difference varying between 0 (purely elastic) and $\pi/2$ (purely viscous), and $\lambda$ is the dynamic module.

Biomechanically, this may be interpreted as that a stronger muscle increases the force resisting the oscillation and thereby "delays" the vibrations measured by the accelerometer. This is equivalent with that a strong muscle is stiffer or "more viscous" than a slack, gelatinous, and "more elastic" muscle.

A general problem in the prior art in the field is that devices, methods, and systems fail to properly apply mechanotransduction therapy and then fail to properly and accurately record the therapy results. For example, patients present with various and unique anatomy. The vaginal canal, or instance, of patients can vary greatly due to genetics, injury, age and the like. Therefore, a therapy device for one patient may not necessarily be the best therapy device for another patient.

Another problem with the prior art is that measurement values are often given in terms of pressure, e.g. in millimeter water column. As pressure is a force divided by an area, the pressure reported will depend on the area of the measuring apparatus, and hence on the supplier. Therefore, in the literature in the field, measurement values are often given in the format '<Supplier_name> mmH20', for example. In turn, this results in that measurement values from different apparatuses are not directly comparable, and consequently a need exists for supplier independent measurement values in the field of the invention.

U.S. Pat. No. 6,059,740 discloses an apparatus for testing and exercising pelvic floor musculature. The apparatus includes an elongate housing adapted for insertion into the pelvic floor aperture. The housing is divided longitudinally into two halves, and includes an oscillator as well as a cut out and equipment for measuring pressure applied to the housing halves from the pelvic floor musculature. The apparatus indicates the force pressing together the two halves in Newton (N), and essentially measures the training effect on muscles acting radially on the housing.

A need exists for an apparatus that may be adapted to various and unique anatomy so that therapy may be properly applied.

Another need exits that measures and trains the musculature running in parallel with a longitudinal direction of the apparatus or pelvic floor opening.

The object of the present invention is to address one or more of the above problems, while maintaining the advantages of prior art.

SUMMARY OF THE INVENTION

According to the invention, this is achieved by an apparatus, system, and method for tissue regeneration.

The present invention includes a housing that is adaptable for a particular site or location of treatment. For instance, the housing may be generally curved or pliable to enable it to be applied to an arm or leg in order to treat the epidermis or skeletal muscle of a patient. The housing may able be generally planar and/or pliable to permit it to be applied to a back, chest or abdomen of a patient in order to treat the back, chest, abdominal epidermis and skeletal muscles.

In another embodiment of the invention, the housing may be generally elongate and selectively adaptable or adjustable prior to or after inserting into an orifice or opening in a patient. Such openings include but are not limited to a pelvic floor opening to treat the pelvic floor muscles or tissue, rectal openings, urethral openings, and openings of the ears, nose and throat. Openings may also include surgical site openings. For instance, during the surgical treatment of internal organs such as the liver, lungs, bladder, kidneys, pancreas, heart, and brain.

The housing may include an adaptable or adjustable exterior that enables it to be selectively adjustable to engage or contact a tissue to be treated. In another example embodiment, the adjustable housing may cause continuity of tissue contact between various layers of tissues in proximity to each other in order to permit effective mechanotransduction therapy through the number of tissue layers.

The housing may include one or more mechanotransduction generators that are capable of creating a tissue regeneration response or environment in the selected tissue. In one example embodiment, the mechanotransduction generator may include an oscillator capable of generating a vibration signal and an accelerometer for reading the vibration signals from the oscillator. The accelerometer may be connected to a signal processor configured for communicating signals representative of values read from the accelerometer.

The use of an accelerometer for measuring a response makes it possible to use a closed housing, simplify the remaining construction, and increase the accuracy of the measurements. It is also possible to calculate a relative amplitude attenuation, phase delay, and/or dynamic modulus in one or more dimensions. These parameters, combined or individually, can be used for characterizing the musculature in a more accurately and detailed manner than is possible with the prior art.

Also, imposing oscillations and/or measuring responses along several axes allow the adaptation of training and testing to specific muscle groups in the pelvis floor.

In another aspect, the present invention relates to a system using such an apparatus with a controller configured for controlling the frequency and/or amplitude of the oscillation. The system is characterized in that it further includes a control module configured for determining an oscillator parameter within at least one time interval, and for providing the oscillator parameter to the controller; a data capturing module configured for receiving a response from the accelerometer and calculating a result as a function of the oscillator parameter and the received response; an analysis module configured for calculating at least one group value based on a series of measurements of oscillator parameters and the results thereof; a data storage configured for storing and retrieving at least one data value from a group consisting of the oscillator parameters, response, calculated result, and group value; and communication means configured for conveying the data value between the modules and the data storage.

In a third aspect, the present invention relates to a method for using mechanotransduction to treat, testing, and exercise tissue, such as the pelvic floor musculature, wherein an oscillation is imposed on the musculature, characterized by measuring the response from the musculature using an accelerometer and characterizing the musculature based on the response to the oscillation imposed.

Suitable measurement parameters, such as the relative amplitude attenuation, phase delay, and/or dynamic modulus, may indicate, among other things, force and/or elasticity of various muscle groups in the pelvic floor.

In a preferred embodiment, the tissue or musculature is imposed an oscillation of a frequency equal or close to the maximum response frequency during training of the musculature. The maximum response frequency is assumed to change over time, and may be, inter alia, displayed and/or logged in order to document training effect, alone or in combination with one or more other parameters.

In another embodiment of the present invention, mechanotransduction therapy applied to the pelvic floor has been shown to foster a regenerative environment, and "jump-start" the proliferation and differentiation of stem cells for various types of tissues. In order for mechanotransduction to be the most effective, there must be enough tension in the pelvic floor to achieve sufficient mechanotransduction signaling. This tension may be achieved by voluntarily contracting the pelvic floor musculature. The tension can be further supplemented if using a barrier, similar to any of the embodiments disclosed herein, which provide a greater surface area for tissue compliance. In one embodiment of the invention, electrodes may be used to cause tissue pre-tensioning.

Additional features and embodiments will be apparent from the attached patent claims.

BRIEF DESCRIPTION OF THE DRAWINGS

The invention will be described in more detail in the detailed description below with reference to the appended drawings, in which.

DETAILED DESCRIPTION

Figure 1A:
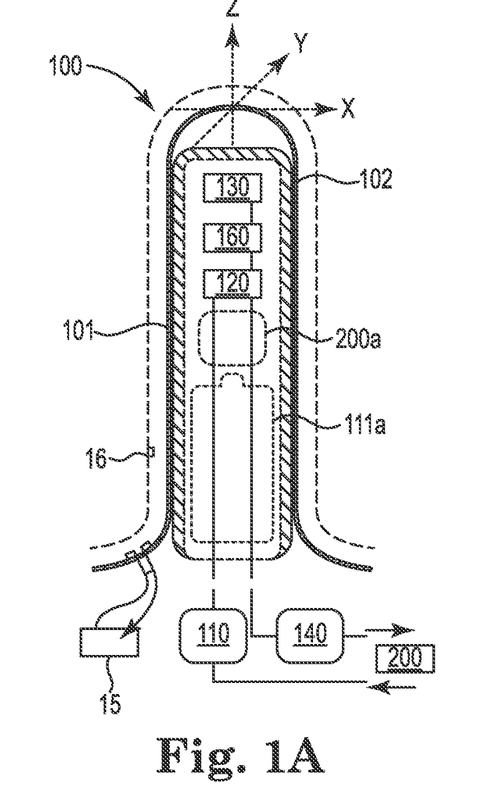
FIG. 1A is a longitudinal schematic section of an apparatus.

FIG. 1A is a longitudinal schematic section of an apparatus 100 according to the invention. The apparatus is comprised of an elongate, cylindrical housing 101, which can be made of a relatively rigid plastic material. Advantageously, an outer casing 102 made of medical silicone can be provided on the outside of housing 101. The size of the housing is adapted for an opening in the pelvic floor.

In an example embodiment of the invention, housing 101 may have a selectively adaptable or adjustable outer casing 102 that enables it to expand to engage or contact a tissue surface to be treated. As particularly illustrated in the example embodiment of FIG. 1A, the outer casing 102 may be expandable between a resting state and an expanded state, which is generally characterized by having a larger circumference and/or length than a in the resting state.

Figure 1B:
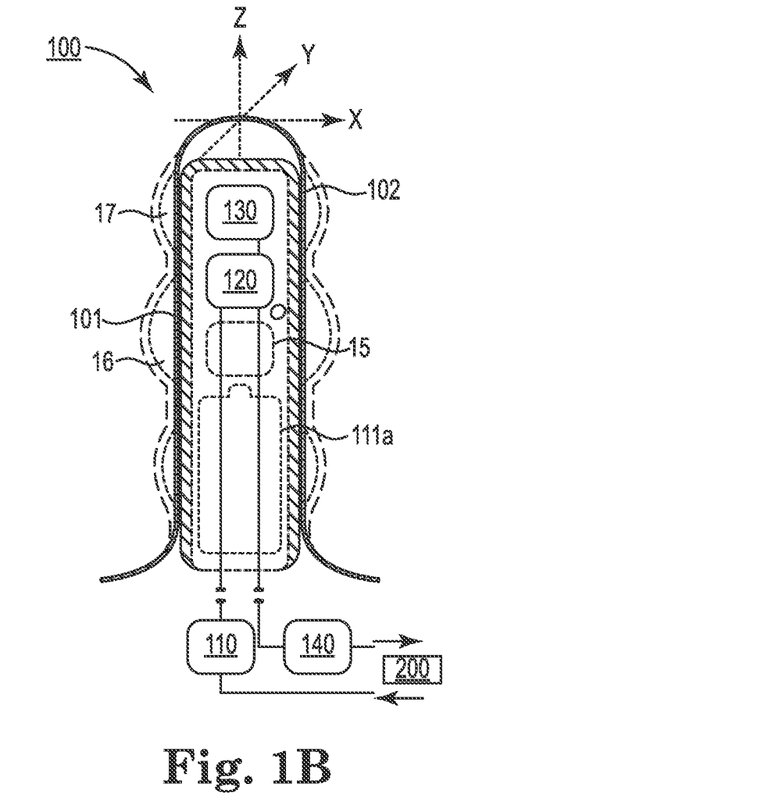
FIG. 1B is a longitudinal schematic section of an apparatus.

Referring to FIG. 1B, housing 101 may include an inflator 15 operatively mounted inside that is in fluid communication with the outer casing 102. Operation of inflator 15 causes air or liquid to enter a space 16 between an inner surface of housing 101 and an inner surface of outer casing 102. Inflator 15 selectively moves apparatus 100 between the resting and expanded states. When the apparatus 100 is in the expanded state it applies a force or stress on proximate tissue such that the tissue may be characterized as being in a pre-tension state. The importance of having a tissue in a pre-tension state will be discussed in more detail below.

The outer casing 102 may be expanded in a uniform manner, as illustrated in FIG. 1A or a generally non-uniform manner, as illustrated in FIG. 1B. A non-uniform expanded state permits the apparatus 100 to be used to treat specific or selective tissue areas. For instance, a patient suffering from urinary incontinence apparatus 100 may expand such that it is capable of pre-tensioning and treating an anterior of the vaginal wall. A patient suffering from urinary incontinence and fecal incontinence would benefit from pre-tensioning and treating the anterior and posterior vaginal walls. Apparatus 100 may include baffles 17 disposed in space 16 that are in fluid communication with inflator 15 such that apparatus 100 may selective inflate certain baffles 17 to causes pre-tensioning of selective tissue(s). Apparatus 100 may also include one or more valves in communication with inflator 15 and baffles 17 to selectively control the baffles 17.

Figure 1C:
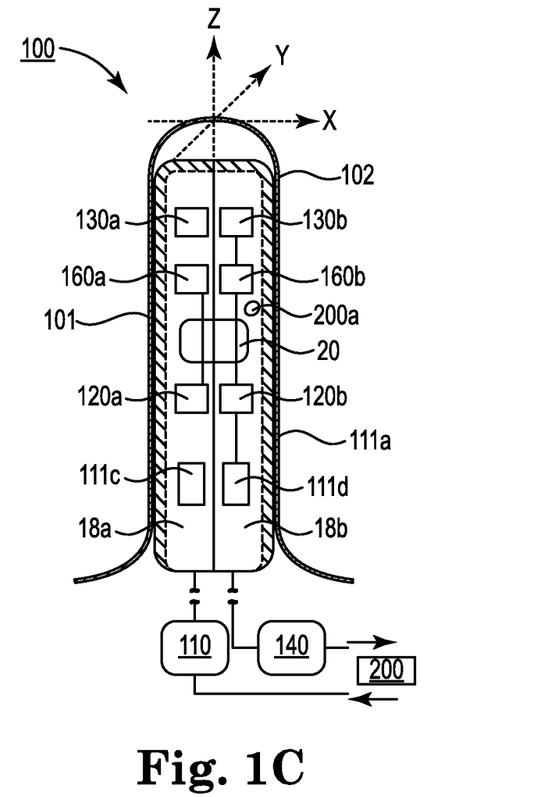
FIG. 1C is a longitudinal schematic section of an apparatus.

Referring to FIG. 1C, in yet another example embodiment of the present invention, there may be one or more separate by operatively coupled inner housing segments 18a and 18b. As particularly illustrated in FIGS. 9A and 9B, an adjustor 20 may be operatively positioned in recesses or bores 22a and 22b extending into each of the housing segments 18a and 18b. The adjustor 20 may comprise any type of mechanism capable of moving housing segments 18a and 18b generally away from each other, such that the diameter or circumference of apparatus 100 is expanded or increased.

Figure 9A:
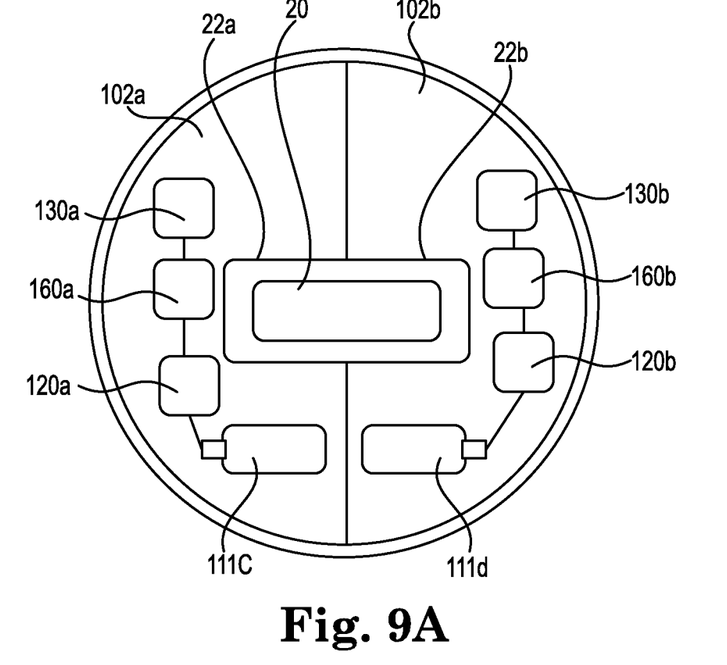
FIGS. 9A-9B illustrate a cross section of an expandable housing.
Figure 9B:
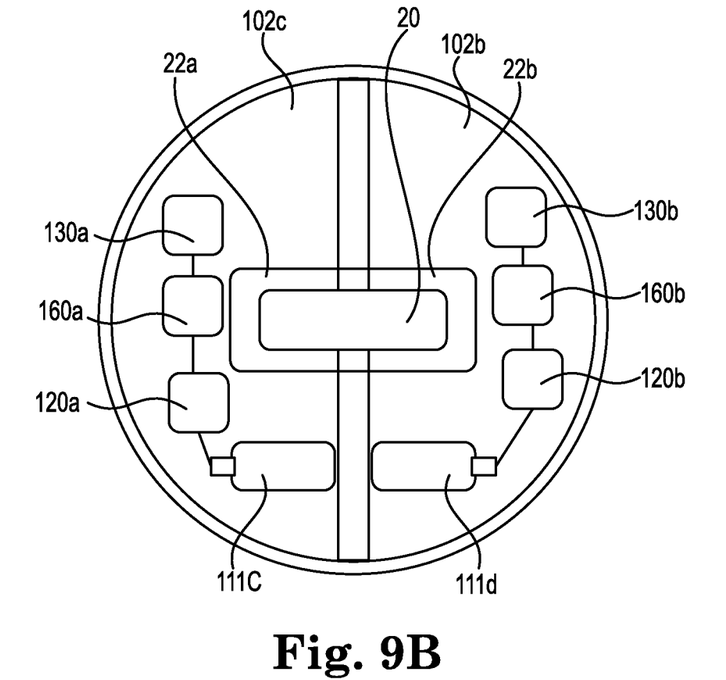

In one example embodiment of the invention, adjustor 20 may comprise a motor having one or more screws associated with each housing segment 18a and 18b. The screws may operate concurrently or separately to move housing segments 18*a* and 18*b* between the expanded and resting states. In another example embodiment of the invention, adjustor 20 may comprise a compressor that utilizes air or a fluid to move housing segments 18*a* and 18*b* between the expanded and resting states. The foregoing is for illustrative purposes only and any type of adjustor may be utilized and any number of housing segments may also be used.

Housing 101 or each housing segment 18*a* and 18*b* may include an oscillator 120 or 120*a* and 120*b*, able to oscillate along one, two, or three axes, and an accelerometer 130 or 130*a* and 130*b* able to measure the acceleration along one, two, or three axes. Preferably, the accelerometer axis or axes is/are aligned with the oscillator axis or axes, for the following reason:

Assume that oscillator 120 or 120*a* and 120*b* effects an oscillation of the apparatus along an axis x, and that the response is measured along an axis x' forming an angle a with the x-axis. If a response along the x-axis is B, then the response along the x'-axis B'=B·cos α. B' has a maximum for cos α=1, i.e. with α=0 and the x'-axis parallel with the x-axis. Correspondingly, B'=0 when the accelerometer axis is perpendicular to the oscillation (cos 90°=0). Thus, by arranging the x-axis of accelerometer 130 or 130*a* and 130*b* in parallel with the x-axis of oscillator 120 or 120*a* and 120*b* we expect the largest possible signal and hence the greatest sensitivity possible. The same is true along the y- and/or z-axes when apparatus 100 has more than one axis. Also, the level of crosstalk between the measured signals is minimized when the axes are perpendicular to each other, e.g. as shown with the x, y, z coordinate system of FIG. 1.

From FIG. 1A it can also be seen that oscillator 120 and accelerometer 130 are offset relative to each other along the longitudinal axis of the apparatus, i.e. the z-axis. Strictly speaking, therefore, they have separate axes in the x direction, e.g. x and x'. However, this has no significance as long as the axes are parallel to each other, cf. the previous section. Hence, for convenience, the x-axes of the oscillator, accelerometer and apparatus are referred to as one axis, "the x-axis". The same applies for the y- and z-axes.

Figure 1D:
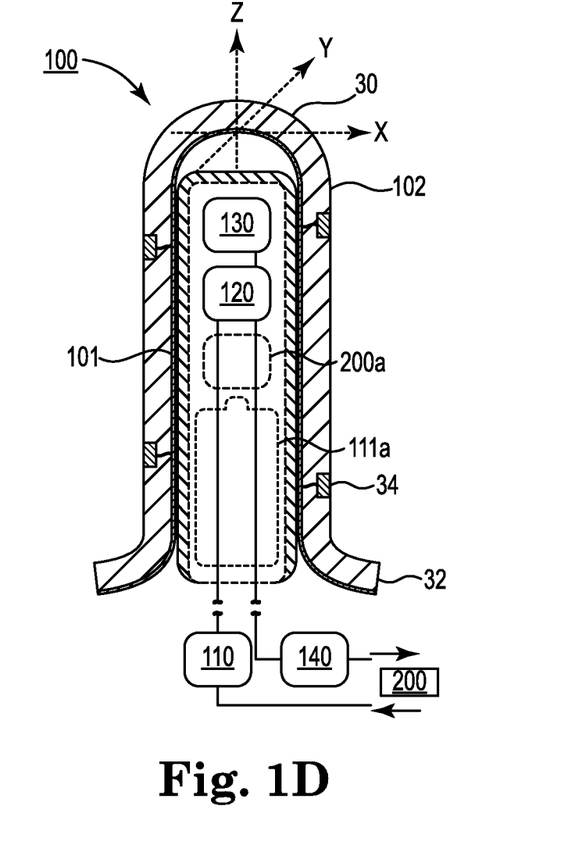
FIG. 1D is a longitudinal schematic section of an apparatus.
Figure 1E:
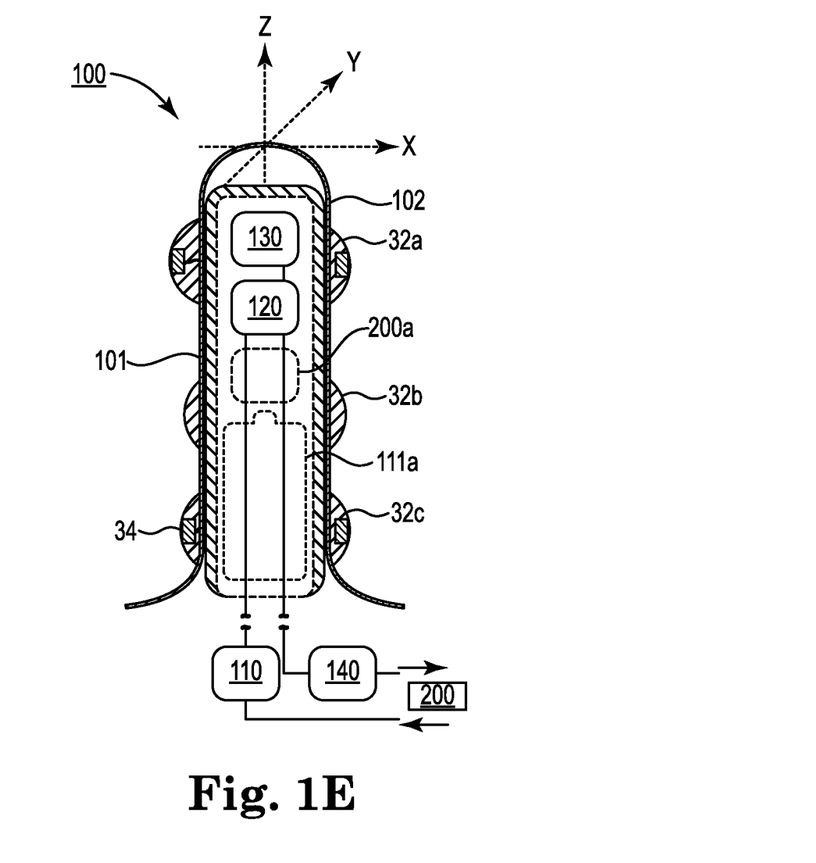
FIG 1E is a longitudinal schematic section of an apparatus.
Figure 2:
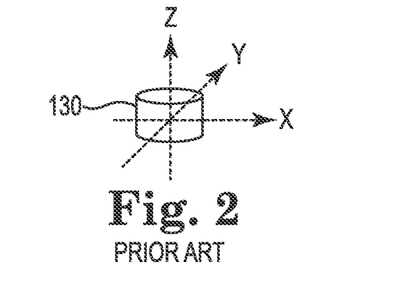
FIG. 2 illustrates alignment of a triaxial accelerometer in the apparatus of FIG. 1A.

FIG. 2 illustrates a triaxial accelerometer 130, having its axes x, y, and z parallel with the axes x, y, and z of the apparatus shown in FIGS. 1A, 1B and 1C. In a preferred embodiment, the frequencies of the oscillations, and optionally also the amplitudes, can be controlled independently of each other along said x, y, and z axes. This makes it possible to measure the strength of a muscle or muscle group running in parallel with the main axis of the apparatus, the z-axis, independently of muscles or muscle groups acting radially on the apparatus along a combination of the x- and y-axes of FIG. 1.

In the following, parameters of one, two, or three dimensions are denoted with boldfaced characters, and the component of a parameter along the x, y, and/or z axis is indexed with x, y, and z, respectively. For example, the frequency ω=(ωx, ωy, ωz). In some embodiments, the three frequency components may have different values, and one or two of the components can be zero, i.e. one or two oscillators could be eliminated. The same applies for a response or out signal a from accelerometer 130 or 130*a* 130*b*, calculated results ΔA, φ·A, and so on.

Components along the x, y, and z axes are measured and calculated independently of each other, e.g. as indicated in eqs. (1) to (4).

The oscillator 120 or 120*a* and 120*b* can be controlled to vibrate with a specific frequency, preferably within the range of 15-120 Hz, by a power supply 110. Alternatively, the oscillator 120 or 120*a* and 120*b* can be driven by a battery 111*a*, 111*c* and 111*d*, shown in FIGS. 1A, 1B and 1C.

Figure 5:
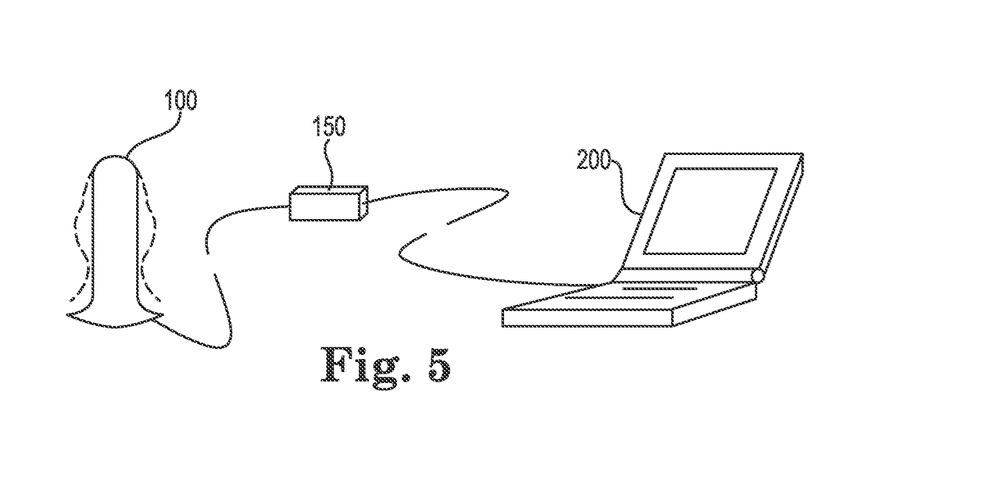
FIG. 5 is a schematic illustration of a system according to the invention.
Figure 6:
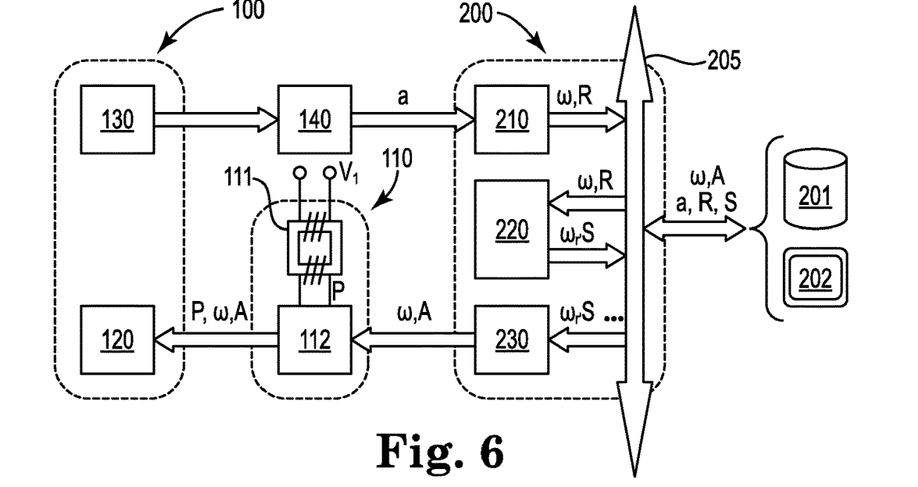
FIG. 6 is a schematic depiction of the functions of the system.

The output signal from accelerometer 130, 130*a* and 130*b* can be passed to a signal processor 140 and thence to a computer 200 (see FIGS. 5 and 6). Alternatively, the entire or parts of the signal and data processing can be performed by a unit 200*a* inside the housing 101.

Oscillator 120, 120*a* and 120*b*, accelerometer 130, 130*a* and 130*b*, and signal processor 140 are commercially available products, and it is within the ability of a person skilled in the art to select models suited for the particular purpose. It is understood that FIGS. 1A, 1B and 1C are principle drawings, and that the connections between the components may include several channels, e.g. one input channel per oscillator axis and one output channel per accelerometer axis. In some applications, accelerometer 130, 130*a* and 130*b* and/or signal processor 140 may be driven by electric power supplied through a USB connection, for example. In other applications, it may be necessary or convenient to have a separate grid-connected transformer 111 in the power supply 110, as shown in FIG. 6.

Figure 3:
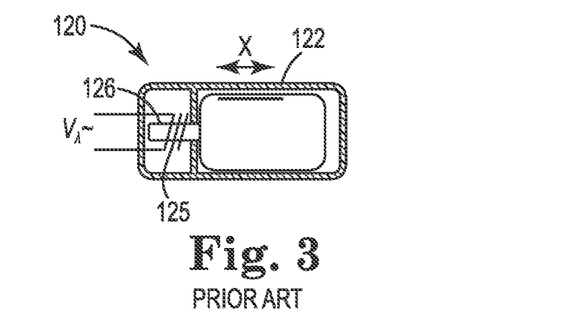
FIG. 3 (prior art) shows the principle of an oscillator.

FIG. 3 illustrates the principle of a possible oscillator 120, 120*a* and 120*b*. The oscillator shown includes a permanent magnet 126 arranged in a coil 125. When an AC voltage Vx is applied to the poles and a current is driven through the coil, a variable magnetic field is induced which drives the permanent magnet 126 back and forth in a reciprocating motion. The permanent magnet 126 is attached to a weight 122 which hence also moves back and forth. When the oscillator is attached to housing 101, the apparatus 100 will oscillate along the x-axis.

Figure 4:
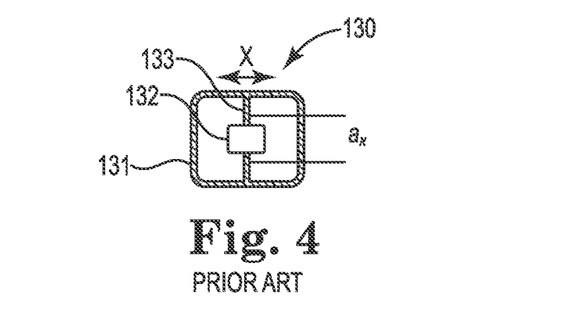
FIG. 4 (prior art) shows the principle of an accelerometer.

FIG. 4 illustrates the principle of a typical accelerometer. A piezoelectric disc or bar 133 is fixedly clamped within a housing 131. The disc 133 retains a seismic mass 132. When the housing is moved back and forth along the x-axis, the disc will be acted on by the mass 132 and an electric charge is produced, typically a few pC/g, on the disc 133 by the piezoelectric effect. For frequencies below about one third of the resonance frequency of the accelerometer housing, this charge will be proportional with the acceleration. The output signal is illustrated schematically as ax in FIG. 4. Commercial vibrational testing accelerometers of this type typically have a frequency range from approx. 0.1 to above 4 kHz, i.e. far outside the range of 15-120 Hz preferred in the present invention.

The present invention does not rely on any specific types of oscillators or accelerometers. For example, eccentric weight oscillators may be used instead of the type shown schematically in FIG. 3. A design of the type shown in FIG. 3 can also be used as an accelerometer: In such a case, weight 122 is moved in dependency of the applied forces. This induces a movement of permanent magnet 126 inside coil 125, and a current is induced that can be read at the poles at Vx FIG. 5 illustrates a system in which a computer 200 controls an oscillator of apparatus 100 through a power supply 110. The computer 200 can be of any design. Suitable computers have a programmable processor, and include personal computers, portable units (PDAs), etc. Computer 200 can be connected to a display, printer, and/or data storage in a known manner for displaying and/or logging measurement results.

Signals from an accelerometer (130 or 130*a* and 130*b*, FIG. 1A, 1B or 1C) of apparatus 100 are amplified and/or processed in a signal processor 140, and transferred to computer 200 for analysis and/or logging. The connection between apparatus 100 and the box 110, 140 may include several channels for controlling oscillators along several axes independently of each other as well as for measuring responses of a uniaxial or multiaxial accelerometer. The same applies for the connection between box 110, 140 and computer 200. This connection may be a USB (2.0 or the like) connection, and, in some applications, electric power may be supplied from the computer through the USB connection.

In some embodiments, signals may be transferred wirelessly (not shown), e.g. by way of radio signals, infrared light, or ultrasonic signals.

Figure 8A:
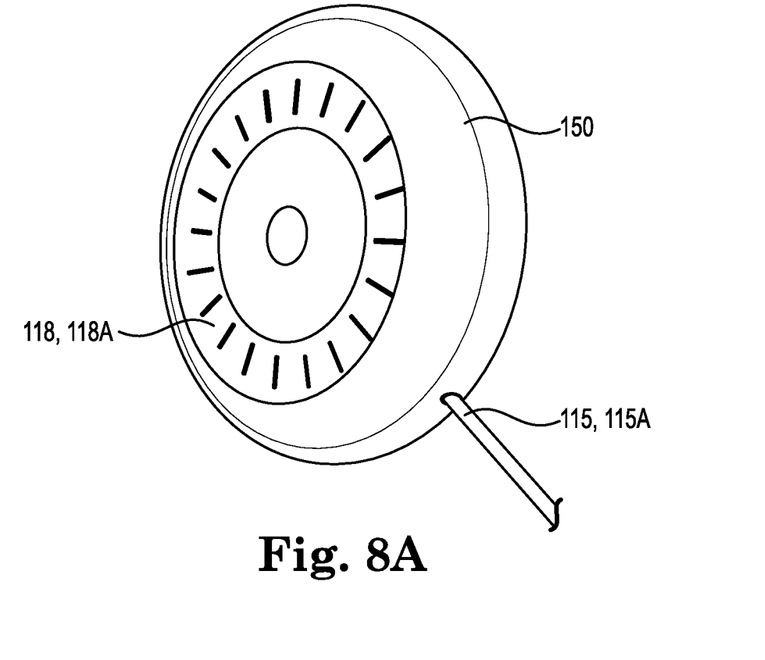
FIGS. 8A-8D illustrate a more detailed embodiment of the signal processor according to the invention.
Figure 8B:
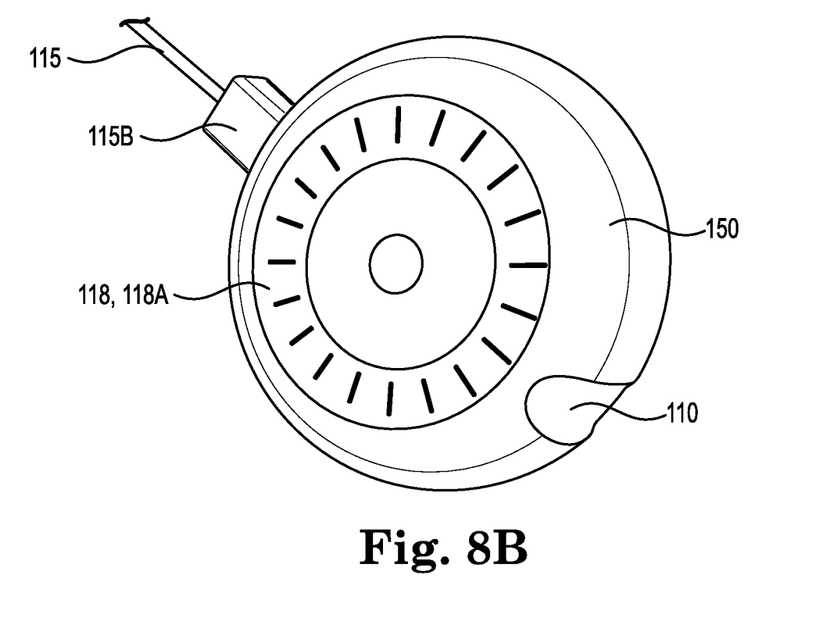
Figure 8C:
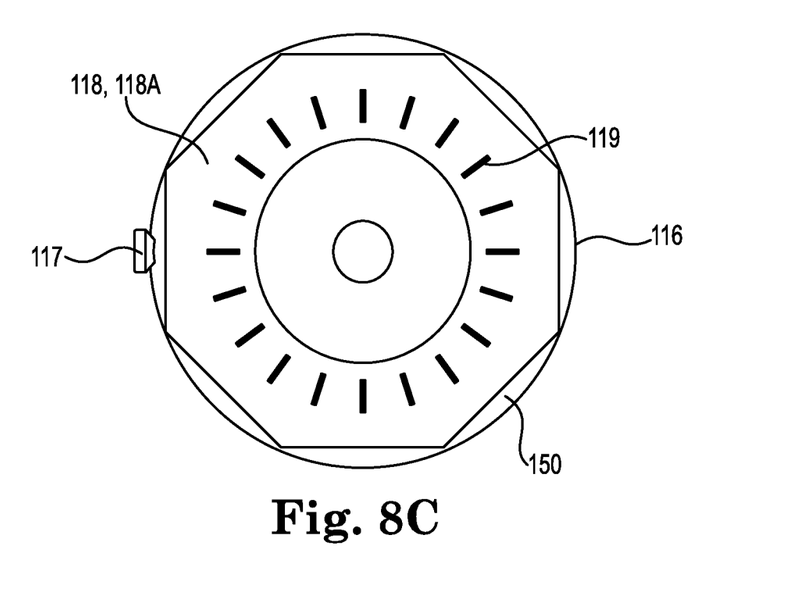
Figure 8D:
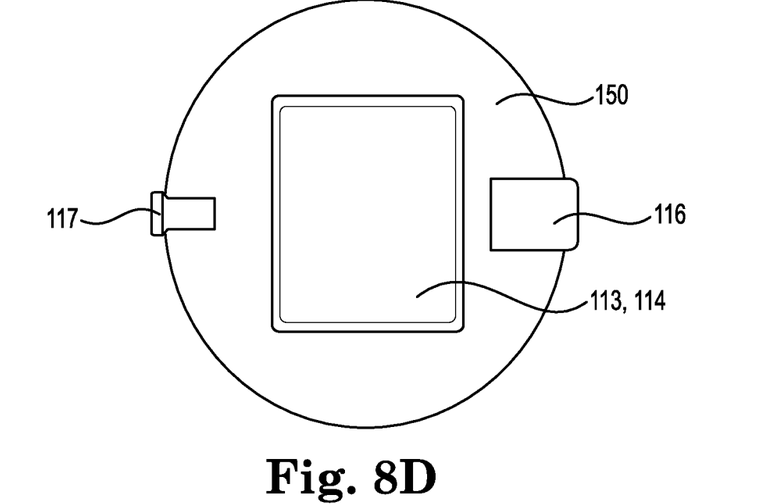

FIGS. 8A-8D show another embodiment of the system, and in particular a more detailed embodiment of signal processor 110, 140, according to the present invention, in which the power supply 110 and signal processor 140 can be embedded into a separate unit or box 110, 140 accommodating at least one rechargeable or replaceable battery or battery package 113 (FIG. 8D).

Signal processor 140 may also include: a CPU including the appropriate software; electronic circuitry programmed with suitable algorithms for managing and controlling the oscillation frequency and optionally the oscillation amplitude; input(s) for at least one EMG sensor (EMG=Electromyography); and input(s) for at least one force sensor. A sensor, such as a force sensor, may be used to measure the amount of pretensioning is applied to the proximate tissue.

The stand-alone unit or box 110, 140 can include a charge input. Additionally to the charge input, or in an alternative embodiment, in which the battery or batteries or the battery package 113 is to be replaced or charged at another location, the stand-alone unit or box 110, 140 may include a cover 114 which can be opened and closed, or the casing (housing) of the unit or one half of the unit or box 110 may be arranged so as to be easily opened and closed (i.e. without the need for using a tool).

The wire 115 from apparatus 100 may be permanently connected 115A to the box 110 of signal processor 140, or, alternatively, may be arranged so as to be pluggable 115B (by means of a plug 115B) into the input port or connector 116 of the unit 110, 140.

Signal processor 140 may further include a loudspeaker and/or display 118 for the instantaneous or immediate biofeedback on muscle activation as observed through the dampening of oscillations and/or force read from the apparatus 100 and/or EMG activity in the muscle acting on apparatus 100. Display 118 may have a suitable shape adapted for the requirements of functionality and placement. An octagonal (eight-sided) 118B, six-sided or round 118A LCD or LED display 118, having about 40 segments 119, for example, could be used. The unit 110, 140 may also include an on/off button 117. In addition, or alternatively, the electronic circuitry of signal processor 140 may be configured so as to switch off after a predetermined time interval of inactivity, e.g. from one to a few minutes of no active use.

Additionally, the stand-alone unit or box 110, 140 may include a CPU device and/or calibration means including at least one of a CPU device and various sensor means to allow, among other things, the calibration of a new apparatus 100 in the system. Unit 110, 140 may also transfer, e.g. wirelessly, real-time data to computer 200 of various reasons.

Apparatus 100 may include an integrated triaxial gyro sensor which, together with the triaxial accelerometer 130, allows the data or signal processor 140 or computer 200 to calculate the 3D orientation of the apparatus 100.

FIG. 6 is a schematic depiction of components of the system illustrated in FIG. 5.

A control module 230, e.g. hardware and software in the computer 200, determines an oscillator parameter, i.e. frequency and/or amplitude, for oscillator 120. When the apparatus is being used for the first time, the control module 230 could set the frequency $\omega$ to a fixed initial value and then increase the frequency in predetermined increments $\Delta\omega$. On subsequent use, control module 230 can use previous results for selecting other initial values and/or frequency intervals. This is described in more detail below. The same applies for the amplitude settings. Alternatively, oscillator parameters could be determined in a binary search which is ended when the values of two consecutively calculated values are closer than a predetermined resolution, e.g. $\Delta\omega x=5$ Hz.

Both frequency and amplitude may be adjusted along the x, y, and z axes independently of each other by means of controller 112. In FIG. 6, controller 112 is connected to a power source in the form of a transformer 111 connected to the grid voltage V1, delivering a power P with the desired current and voltage. As shown in FIG. 1, in the alternative, the power source could be a battery 111a located inside the housing 101 of the apparatus. For example, the controller 112 may control the amplitude Ax and frequency $\omega x$ of the oscillator by controlling the current, voltage, and frequency of the signal supplied at the poles Vx of FIG. 3, and in a similar manner for oscillators oscillating along the y and/or z axes.

The oscillation is imposed on tissue surrounding apparatus 100, and the response is measured by accelerometer 130 or 130a and 130b.

Signals from accelerometer 130 or 130a and 130b of apparatus 100 are passed to a signal processor 140, which is provided as a separate box including an array of accelerometers. Accelerometer 130 or 130a and 130b may include a preamplifier, and unit 140 may include a pre-amplifier. Other configurations are possible as well. The output signal from signal processor 140 is shown as a, and may represent, for example, acceleration along the x, y, and/or z axes at a measurement point at which the imposed oscillation was on.

A data capturing module 210 process the signal further, and may, for example, integrate an acceleration to obtain a velocity and once more to obtain a displacement, measure a phase difference, etc. Said integration of acceleration, measurement of phase difference, etc. may be carried out at several locations in the signal path using feedback operational amplifiers, firmware, and/or software, for example, in a known manner. Note that the signal path of FIG. 6 is exemplary only.

Output data from the data capturing module 210 are shown schematically as a measurement point $\omega$, R, at which a result R is measured or calculated at an applied frequency $\omega$. The result R may represent one or more of: acceleration a, velocity, displacement, relative amplitude attenuation $\Delta A$, phase shift, stress, strain, and/or dynamic modulus as discussed above. In some applications, the oscillator amplitude may also be varied. Advantageously, the data capturing module can store a measurement sequence including a series of measurement points each representative of an oscillator parameter to or A and a measured or calculated result R. As used herein and in the claims, the term "data values" is understood to mean any parameter value and/or the components thereof along the x, y, and/or z axes.

A data bus 205 carries data values between various components and modules of computer 200. For example, a measurement series with a sequence of measurement points ($\omega i$, $R_i$) can be temporarily be stored in a data storage 201 before the measurement series is further processed in an analysis module 220. In another embodiment, the measurement points (ωi, R;) could be passed to analysis module 220 at a later point, and the processing results, represented by (ωr, S), could be stored in data storage 201 and/or displayed on a display means 202.

Analysis module 220 is a module processing one or more measurement series to characterize the musculature and the development thereof using one or more parameters deemed suitable.

In a preferred embodiment, a maximum response frequency cur is obtained for each measurement series. The maximum response frequency cur is the value of the imposed frequency for which the measurement parameter selected indicated a maximum response from the tissue surrounding the apparatus, such as the maximum amplitude attenuation, minimum amplitude measured, largest dynamic modulus, etc. This is discussed in more detail below.

In principle, analysis module 220 may calculate any desired group value and/or carry out statistical analysis of the acquired data, such as statistical distributions, mean or expected value, variance, maximum values, and trends in the development of the measured and calculated results described above, for example.

In one embodiment, for example, the group value S may represent a subinterval of the range of 15-120 Hz within which the maximum response frequency air is located with a given probability. This interval may be calculated as a confidence interval from earlier measurement series using known statistical methods, and is expected to become smaller as the number of measurement series increases and the variance hence reduces. The purpose of calculating such a subinterval is to avoid superfluous measurements.

An exemplary trend analysis is the development of the maximum response frequency air over a few days or weeks, which may provide information on training effect.

Figure 7:
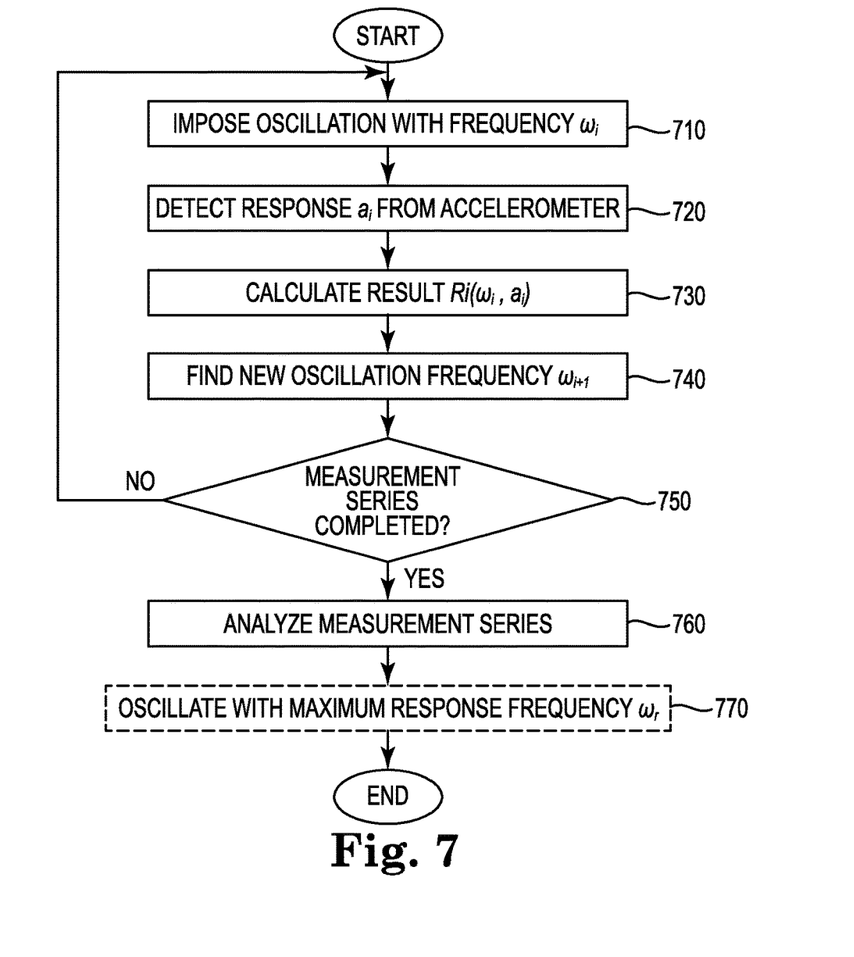
FIG. 7 is a flow diagram illustrating a method according to the invention.

FIG. 7 illustrates a method according to the invention.

In block 710, the musculature is imposed a first oscillation represented by ωr. In practice, this can be accomplished by introducing an apparatus as described above into a pelvic floor aperture and supply the oscillator 120 with electric power. The oscillation may be imposed along one or more mutually orthogonal axes (x, y, z). At the first use, the initial value could be about 15 Hz, for example, along each axis. After the apparatus has been used one or more times the initial values may be based on previous results and analyses.

In block 720, the response ai, from the tissue or musculature is measured by means of an accelerometer 130, 130a or 130b having axes oriented in parallel with the oscillator axes x, y, and/or z.

Block 730 illustrates that a result Ri is found from an imposed oscillation on and its response a; as measured in a predetermined time interval. The measurement point (ωi, Ri) may be part of a measurement series in which i=1, 2, ... n, and each index i represents a separate time interval. Both the imposed frequency and the measured or calculated result have distinct values along the oscillator axes. Results suitable for characterizing the musculature may be the relative amplitude attenuation ΔA, dynamic modulus λ, and/or phase shift φ between the applied and measured signals. The values may be measured and/or calculated as set out above in connection with eqs. (1) to (4), and independently of each other along the axis or axes x, y, and/or z. The measurement point (ωi, Ri) can be stored or logged as part of this step.

In block 740 an oscillation frequency for the next measurement point is calculated, and in determination block 750 a determination is made whether the measurement series has been completed.

In a first embodiment of the method, the imposed frequency is incrementally increased in block 740, for example according to ωi,=ω0+i. Δω, where Δω denotes a desired resolution for the measurement series, such as 1 Hz or 5 Hz. In this case, the loop ends in determination block 750 when the new frequency Δωi+1 exceeds a predetermined threshold, e.g. 120 Hz, along the axis or axes.

In an alternative embodiment of the method, the objective is to find a maximum response using the smallest number of measurements possible. This may be carried out efficiently by way of a binary search. For example, assume that the result R from block 730 increases with the response of the musculature to the imposed oscillations, that a first interval is 15 Hz to 120 Hz, and that the desired resolution is 5 Hz along each axis. In this case, the binary search can be performed by bisecting the interval, rounding the frequency down to the nearest integer frequency divisible with the resolution, and compare the results of block 730 for each of the two frequencies in the upper and lower parts of the interval, e.g. R1 at ω1=15 Hz and R2 at ω2=50 Hz. If R2>R1, ω3 is selected as the center of the interval 50-120 Hz in block 740, otherwise ω3 is selected as the center of the interval 15-50 Hz in block 740. Similar bisection of the intervals is repeated in this alternative embodiment until determination block 750 indicates that the next interval is narrower than the desired resolution, e.g. 5 Hz along each axis.

If the responses along the axes are independent of each other, a binary search in the interval 15-120 Hz with a resolution of 5 Hz along each axis will be able to find an approximate maximum response frequency using at most 6 measurement points, whereas a sequential search in the interval 15-120 Hz with a resolution of 5 Hz would require 21 measurement points.

If determination block 750 indicates that the measurement series has not been completed, a new iteration is performed in which block 710 imposes an oscillation with a new frequency Δωi+1, etc. When determination block 750 indicates that the measurement series has been completed, the process proceeds to block 760.

In block 760 one or more measurement series is analyzed as described for analysis module 220 above. In a preferred embodiment, the maximum response frequency ωr is calculated for each measurement series. By definition, this is the frequency at which the musculature responds most strongly to the imposed oscillation. In practice, the maximum response frequency can be rounded down to the nearest integer frequency which is divisible with the resolution, i.e.

$$\omega_r = \Delta\omega \cdot \text{round}(\omega_r' / \Delta\omega), \quad (5) \text{ where}$$

$\omega_r$ is the practical value of the maximum response frequency, $\omega_r'$ is the theoretical or ideal value of the maximum response frequency, Δω• is the resolution chosen, e.g. 5 Hz as in the above example, and round( ) is a function which rounds down to the nearest integer.

Block 770 has been drawn with dashed lines to illustrate that the method may, but does not necessarily, include controlling the oscillator to impose the practical value for the maximum response frequency while a user performs pelvic floor exercises as described in the introductory section. Hence, in a preferred embodiment, the resolution Δω should be selected so that the difference between the practical and actual values is of little or no significance. For example, if it turns out to be a telling difference between training with an imposed oscillation of 62 Hz as compared to 60 Hz, Δω in the above example should be reduced from 5 Hz to 1 Hz.

The method may further include storing and/or displaying one or more oscillation parameters, measurement values, calculated results, and/or group values. Each data value may be stored in a data storage 201 and displayed on a monitor 202. It is also possible to log parameters by printing them on paper. Hence, a printer (not shown) may optionally be used instead of or in addition to data storage 201 and display 202 (e.g. a monitor) shown in FIG. 6.

The method described above may further include analyzing the measured and calculated results using known statistical methods. In one embodiment, the development of the maximum response frequency and/or other results over time, for example, may document the training effect. Also, in the present or other applications, a confidence interval for air can be estimated which is smaller than the entire measurement interval, e.g. 15-120 Hz, but still large enough for the probability p that the maximum response frequency is located within said interval to be larger than a predetermined value, such as p>95%.

This may reduce the number of measurement points in the next measurement series, which may be recorded one or a few days later, for example, and stored in data storage 201 (FIG. 6). Data storage 201 may store several such measurement series recorded during a time period, e.g. one measurement series per day for 1-4 weeks, and/or only the particular frequency air within each measurement series which resulted in, for example, the maximum amplitude attenuation or phase shift.

Naturally, statistical analysis, trend analysis, etc. may be performed on one or more measured or calculated results, not only on the frequency as described above. The expression "calculating group value", as used in the patent claims, is intended to include any known types of statistic analysis, trend analysis as well as other forms of analysis performed on one or more measured or calculated results, stored, for example, as measurement series of measurement points (ωi, Ri;) in data storage 201.

During use, it is not uncommon to encounter a patient with tissue or muscle that lacks a preferred amount of tension. For instance, after a woman gives birth it is not uncommon for her vaginal tissue to exhibit less viscoelasticity. In these cases, it may be beneficial to pre-tension the tissue or muscle prior to applying mechanotransduction therapy.

In the embodiments of the invention discussed above, a user or practitioner may insert apparatus 100 into the patient's vaginal opening. Apparatus 100 may be operated to cause outer casing 102 to expand. In other embodiments, adjuster 20 may be operated to cause housing segments 18a and 18b to move from the resting state toward the expanded state. The outer casing 102 or housing segments 18a and 18b can be adjusted until a desired amount of pre-tension is applied to the tissue.

With the tissue or muscle in the pre-tension state, mechanotransduction therapy (described above) may be applied to the tissue or muscle. The pre-tensioning permits the therapy to be more effectively transmitted through the tissue cells to create a tissue regenerative environment.

As the patient continues therapy, her tissue or muscle will begin to become more viscoelastic and the amount of pre-tensioning may be reduced accordingly.

The above should not be considered to be limited to the treatment of vaginal incontinence but may be used for the treatment of any tissue, muscle or organ. For instance, it is within the spirit and scope of the invention to include an apparatus that is capable of being applied to a patient's chest for mechanotransduction therapy of the chest tissue, muscles, lungs or heart.

In yet another embodiment of the invention, apparatus 100 may be reduced in size such that it may be insertable into a patient to apply mechanotransduction therapy proximately or directly to an internal tissue, muscle or organ. For instance, it is possible to have an apparatus small enough to be inserted through a peripherally inserted central venous catheter to apply therapy directly to the heart.

In still another embodiment of the present invention, as illustrated in FIGS. 1D and 1E, pre-tensioning of a patient's tissue may be accomplished by inserting housing 101 into a sleeve 30 that may be used to expand all or a portion of the circumference of the housing 101. The sleeve 30 may have a constant or varying thickness and may vary to accommodate a patient's anatomy. The sleeve 30 may have an opening 31 disposed on an end for receiving the housing 101. The sleeve 30 may have an open or closed end opposite the opening 31.

Referring to FIG. 1E, the sleeve 30 may comprise one or more rings 32a, 32b and 32c. The rings 32a-32c may be connected or separate and may be placed in any desirable location on housing 101. The rings 32a-32c may have any shape conducive to targeting particular anatomical features. For instance, the rings 32a-32c may have a generally curved, ribbed, or undulating outer surface. Other configurations are also possible and should be considered to be within the scope of the present invention.

The sleeve 30 and rings 32a-32c may be manufactured from a material that is capable of transmitting the mechanotransduction vibrations to the tissue of the patient. In one embodiment, the sleeve 30 or the rings 32a-32c may be manufactured from a pliable material like silicone and the like or a rigid or semi-rigid material such as any known or unknown polymer.

In another embodiment of the invention, the pre-tensioning of the tissue may be accomplished by activating one or more electrodes or stimulators 34 coupled to or mounted in/on housing 101, sleeve 30 or rings 32a-32c. The stimulators 34 can emit electrical stimuli that causes the proximate tissue to contract. The contraction of the tissue may be accomplished by a number of mechanisms, including causing the stiffening of tissue substrate. Once the proximate tissue is stimulated and pre-tensioned the mechanotransduction therapy may be applied, which results in improved vibrations being transmitted through the tissue. The stimulators 34 may be in operative communication with a power source disposed in or external to the housing 101.

The stimulators 34 may also be applied to the embodiment used for application of internal mechanotransduction therapy.

Various figures and descriptions disclose features and accessories. However, it must be noted that these features are merely illustrative in nature and may be placed in varying locations and under varying configurations and shapes, and still be consistent with the present invention. In addition, the shape and configuration for the various portions are also merely illustrative and can be altered without deviating from the spirit and scope of the present invention.

In another embodiment of the invention, the disclosed mechanotransduction therapy is combined with stem cells to treat various medical conditions. In this embodiment, stem cells may be introduced into a location of a patient by use of a needle and syringe and then the mechanotransduction therapy disclosed herein may be applied to stimulate the stem cells to differentiate into parts of the cell.

The present invention may be embodied in other specific forms without departing from the spirit or essential attributes thereof, and it is, therefore, desired that the present embodiment be considered in all respects as illustrative and not restrictive. Similarly, the above-described methods and techniques for forming the present invention are illustrative processes and are not intended to limit the methods of manufacturing/forming the present invention to those specifically defined herein.

What is claimed is:

1. An apparatus for regenerating a tissue volume, the apparatus comprising:
a housing having an interior, the housing having an expandable casing configured to expand from a resting state outwardly toward an expanded state wherein the casing in the expanded state is adapted to pretension and apply a stress to the tissue prior to application of an oscillatory therapy;
an oscillator operatively positioned in the interior of the housing and capable of generating and imparting oscillations on cells of the pretensioned tissue;
an accelerometer operatively positioned in the interior of the housing, the accelerometer being adapted to read a change in a volume of the cells of the tissue; and
signal processor configured for receiving a signal from the accelerometer and determining a visco-elastic property of the tissue, wherein the signal processor reads a change in an amplitude signal generated by the accelerometer and the change in the amplitude signal correlates to a visco-elastic property of the tissue;
wherein pretensioning the tissue increases a number of oscillations being propagated through the cells.

2. The apparatus of claim 1, wherein the housing has a smaller circumference in the resting state for insertion and a larger circumference in the expanded state than the resting state to pretension the tissue prior to the oscillator imparting oscillations on the cells, wherein an amount of pretensioning is adjustable.

3. The apparatus of claim 2, further comprising an adjustor in fluid communication with the casing and adapted to expand the casing to pretension the tissue.

4. The apparatus of claim 3, further comprising baffles operatively disposed between the casing and the housing, wherein the fluid flows into the baffles to inflate at least a portion of the casing.

5. The apparatus of claim 1, wherein the housing comprises one or more housing segments, the housing segments being adapted to expand away from each other to pretension the tissue.

6. The apparatus of claim 5, further comprising a motor in operative communication with the housing, the motor being adapted to move the housing segments away from each other.

7. The apparatus of claim 1, wherein the housing comprises an electrical stimulator operatively disposed thereon, the electrical stimulator of the housing being adapted to stimulate the tissue, wherein the stimulation pretensions the tissue.

8. An apparatus for regenerating a tissue volume, the apparatus comprising:
a housing having an interior, the housing being positionable proximate tissue to be treated;
a sleeve having an interior adapted to receive at least a portion of the housing, the sleeve being adapted to move from a resting state for insertion into an opening and an expanded state to pretension the tissue, wherein an amount of pretensioning is adjustable;
an oscillator operatively positioned in the interior of the housing and capable of generating and imparting oscillations on cells of the tissue;
an accelerometer operatively positioned in the interior of the housing, the accelerometer being adapted to read a change in a volume of the cells of the tissue; and
signal processor configured for receiving a signal from the accelerometer and determining a visco-elastic property of the tissue, wherein the signal processor reads a change in an amplitude signal generated by the accelerometer and the change in the amplitude signal correlates to a visco-elastic property of the tissue;
wherein pretensioning the tissue prior to application of oscillations increases a number of oscillations being propagated through the cells.

9. The apparatus of claim 8, wherein the sleeve further comprises one or more rings space apart along a length of the housing.

10. The apparatus of claim 8, wherein the sleeve comprises one or more electrical stimulators operatively disposed thereon, the electrical stimulator of the sleeve being adapted to stimulate the tissue, wherein the stimulation pretensions the tissue.

11. The apparatus of claim 8, wherein the sleeve has a uniform thickness to uniformly pretension the tissue proximate the housing.

12. The apparatus of claim 8, wherein the sleeve has a non-uniform thickness to enable non-uniform pretensioning of the tissue proximate the housing.

13. The apparatus of claim 8, further comprising a display operatively coupled to the apparatus to display an indication of the volume of the cell.

14. The apparatus of claim 13, wherein the display is at least one selected from the group of a visual display, an audio display, or a combination of a video display and an audio display.

15. A method for increasing tissue volume, the method comprising the steps of:
providing a housing having an interior containing an oscillator and an accelerometer operatively disposed therein;
controlling the housing to move from a resting state, wherein it is insertable into an opening, to an expanded state to tighten the tissue and place the tissue in a pretension state;
imposing, with the oscillator, a controlled oscillation on the pretension tissue for testing and increasing a volume of cells of the tissue;
measuring an amplitude signal response from the tissue using the accelerometer;
characterizing, with a signal processor, the volume of the cells of the tissue on an attenuation of the amplitude signal response to the imposed controlled oscillation; and
controlling the controlled oscillation from the oscillator with respect to the amplitude signal response measured by the accelerometer.

16. The method of claim 15, wherein controlling the housing comprises expanding an outer casing to apply a force against the tissue to, thereby pretensioning the tissue.

17. The method of claim 15, wherein controlling the housing comprises moving one or more housing segments away from each other to press against and pretension the tissue.

18. The method of claim 17, further comprising the steps of:
- a) determining an oscillator parameter in at least one time interval;
- b) effecting an oscillation using the oscillator parameter in the time interval;
- c) obtaining a result as a function of the oscillator parameter and the measured response;
- d) repeating steps a) to c) in a measurement series with several discrete time intervals; and
- e) calculating at least one group value based on the measurement series of the oscillator parameters and results thereof.

19. The method of claim 18, wherein the result as the function of the oscillator parameter and the measured response is a relative amplitude attenuation between applied and measured signals.

20. The method of claim 15, further comprising the step of providing a display configured for displaying a measured response.

\* \* \* \* \*